United States Patent
Loesel et al.

(10) Patent No.: US 8,444,633 B2
(45) Date of Patent: May 21, 2013

(54) SYSTEM AND METHOD FOR ALTERING INTERNAL STRESS DISTRIBUTIONS TO RESHAPE A MATERIAL

(75) Inventors: Frieder Loesel, Mannheim (DE); Josef F. Bille, Heidelberg (DE)

(73) Assignee: Technolas Perfect Vision GmbH (DE)

( * ) Notice: Subject to any disclaimer, the term of this patent is extended or adjusted under 35 U.S.C. 154(b) by 1205 days.

(21) Appl. No.: 12/104,401

(22) Filed: Apr. 16, 2008

(65) Prior Publication Data

US 2009/0264873 A1    Oct. 22, 2009

(51) Int. Cl.
*A61F 9/008*    (2006.01)

(52) U.S. Cl.
USPC ............................... 606/5; 128/898

(58) Field of Classification Search
USPC ............................... 606/5; 128/898
See application file for complete search history.

(56) References Cited

U.S. PATENT DOCUMENTS

| | | | |
|---|---|---|---|
| 4,391,275 A | 7/1983 | Fankhauser et al. | |
| 4,718,418 A | 1/1988 | L'Esperance, Jr. | |
| 4,770,172 A | 9/1988 | L'Esperance, Jr. | |
| 4,887,592 A | 12/1989 | Loertscher | |
| 5,920,373 A * | 7/1999 | Bille | 351/212 |
| 6,129,722 A * | 10/2000 | Ruiz | 606/5 |
| 6,210,401 B1 | 4/2001 | Lai | |
| 6,325,792 B1 * | 12/2001 | Swinger et al. | 606/4 |
| 6,984,227 B2 | 1/2006 | Munnerlyn et al. | |
| 2003/0208190 A1 * | 11/2003 | Roberts et al. | 606/5 |
| 2004/0044355 A1 | 3/2004 | Nevyas | |

* cited by examiner

*Primary Examiner* — Bill Thomson
*Assistant Examiner* — Jeffrey Lipitz
(74) *Attorney, Agent, or Firm* — Nydegger and Associates

(57) ABSTRACT

A system and method for altering the configuration of a transparent material (e.g. the cornea of an eye) requires identifying local stress distribution patterns inside the material. These patterns are then used to define boundary (interface) surfaces between volumes within the material. In operation, a laser unit performs Laser Induced Optical Breakdown (LIOB) along selected boundary surfaces to disrupt stress distribution patterns between volumes of the material that are separated from each other by the boundary surface. This LIOB allows an externally applied force to thereby alter the configuration of the material.

20 Claims, 2 Drawing Sheets

SYSTEM AND METHOD FOR ALTERING INTERNAL STRESS DISTRIBUTIONS TO RESHAPE A MATERIAL

FIELD OF THE INVENTION

The present invention pertains generally to systems and methods for performing ophthalmic laser surgery. More particularly, the present invention pertains to laser systems that weaken corneal tissue over selected surfaces inside the cornea. The present invention is particularly, but not exclusively, useful as a system and method for weakening corneal tissue on selected boundary surfaces between tissue volumes, where the surfaces have been identified by abnormal deviations in stress distributions.

BACKGROUND OF THE INVENTION

From a mechanical perspective, the cornea of an eye includes a Bowman's membrane that has exceptionally good tensile strength. Anatomically, Bowman's membrane is a relatively thin layer of tissue that is located just under the epithelium on the anterior surface of the cornea. More specifically, Bowman's membrane extends across the cornea, and its peripheral edge connects with the sclera. Most corneal tissue, however, is not in Bowman's membrane. Instead, it is in the stroma, which is tissue that lies immediately under (posterior) Bowman's membrane. In comparison with Bowman's membrane, although the stroma has significantly more tissue, it has substantially less structural strength.

In the eye, behind (posterior) the cornea is the aqueous humor. Aqueous humor is a clear fluid that fills the space between the lens and the cornea. Importantly, the aqueous humor exerts an intraocular pressure (IOP) against the posterior surface of the cornea. Reactive forces against this IOP are provided by both Bowman's membrane and the stroma.

It can happen for any of various reasons that, during the physical development of an eyeball, the anterior surface of the cornea will sometimes be formed with superficial irregularities, such as topographical depressions or bulges. Moreover, these irregularities persist under the influence of biomechanical forces that develop mostly in the stroma. In more detail, the biomechanical forces that naturally result in the stroma, in reaction to IOP, develop stress distribution patterns that maintain the topography of the eye's anterior surface, with or without irregularities. When irregularities are present, however, the consequences are the creation of optical aberrations. As is well known, these aberrations can be corrected (eliminated or minimized) by returning the anterior surface of the cornea to a normal, substantially spherical shape.

In light of the above, it is an object of the present invention to provide a system and method wherein existing biomechanical forces in the stroma are weakened to disrupt their stress distribution patterns, and thereby allow IOP to reshape the eye's anterior surface. Another object of the present invention is to provide a system and method wherein the location of stress distribution patterns in the stroma are determined and targeted for disruption with reference to deviations in the topography of the eye's anterior surface. Still another object of the present invention is to provide a system and method wherein topographical deviations from a reference datum identify tissue volumes under the deviation, and Laser Induced Optical Breakdown (LIOB) is performed on boundary surfaces of the underlying volume to disrupt stress distribution patterns. Yet another object of the present invention is to provide a system and method for altering a configuration of a transparent material (e.g. a cornea) that is easy to use, is simple to implement and is comparatively cost effective.

SUMMARY OF THE INVENTION

In accordance with the present invention, a system and method for altering the configuration of a transparent material (e.g. the cornea of an eye) requires disrupting stress distribution patterns inside the material. In response to these disruptions, the material reacts to an externally applied force (e.g. IOP) for reconfiguration of the material. Preferably, the required disruptions of stress distribution patterns result from the Laser Induced Optical Breakdown (LIOB) of the material (e.g. stromal tissue in the cornea).

For ophthalmic surgery, it is known that stress distribution patterns inside the cornea of an eye can be located by measuring the topography of the cornea's anterior surface. For this purpose, corneal topography can be measured using a diagnostic device, such as a topography sensor. The measured topography can then be compared with a reference datum to identify deviations between the topography and the reference datum. In turn, the deviations are used to locate the stress distribution patterns. Typically, deviations will be manifested as depressions or bulges that form on the cornea's anterior surface. In any case, a deviation will be an indicator of an underlying abnormal stress distribution.

As envisioned for the present invention, the reference datum represents a desired corneal configuration that will give the desired vision correction. In most cases, the reference datum will be a substantially spherical surface. For the specific case of ophthalmic surgery, deviations from the reference datum will identify areas on the anterior surface of the cornea where superficial changes in the cornea are required. Also, and importantly for the present invention, deviations can be used to identify an underlying volume of material (e.g. stromal tissue). Further, this underlying volume of material will define a boundary (interface) surface that separates the underlying volume from adjacent volumes of material.

For the present invention, a laser unit is used to cut material (stromal tissue) on the boundary (interface) surface of the underlying volume. The extent and scope of this cut will be determined by the extent and scope of the deviation that is used to identify the underlying volume. As for the shape of the cut, depending on the particular reconfiguration that is desired, the cut may be a planar cut or a cylindrical cut. The cut may also be otherwise customized for the particular requirements of the procedure. For example, a predictive model as disclosed in U.S. application Ser. No. 12/016,857 for an invention entitled "Finite Element Modeling of the Cornea," which is assigned to the same assignee as the present invention, can be used for this purpose. In any event, as noted above, the cuts are intended to disrupt the stress distribution on the boundary (interface) surface between material in the underlying volume and adjacent material. More specifically, the cuts may be made on only portions of a tissue volume boundary and may be made on the boundaries of more than one volume. The consequence is that the external force (e.g. intraocular pressure "IOP") will then alter the configuration of the transparent material in response to the weakening of the material that has been cut.

In an alternate embodiment of the present invention, the internal stress distributions can be identified by any of various devices known in the pertinent art. In each case, however, it is important to identify boundary (interface) surfaces that separate volumes in the material from each other. LIOB can then be performed on the boundary surfaces, or portions of the boundary surfaces, as indicated above.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
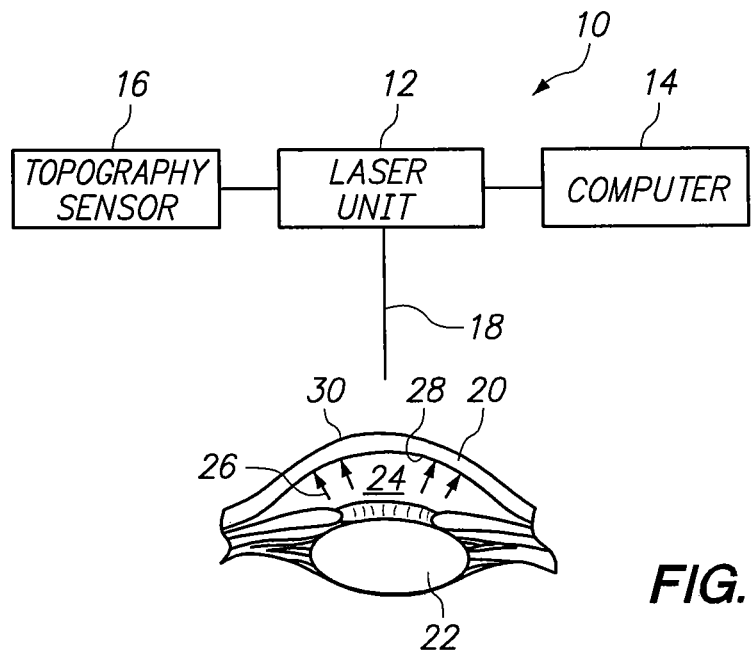
FIG. 1 is a schematic presentation of a system in accordance with the present invention, with the system shown in its intended operational relationship with the anterior portion of an eye.

Referring initially to FIG. 1, a system in accordance with the present invention is shown and is generally designated 10. As indicated and shown, the system 10 includes a laser unit 12, that is electronically connected to a computer 14, and to a topography sensor 16. For purposes of the present invention, the laser unit 12 is preferably of a type that can generate a laser beam 18 that is characterized by femtosecond pulses. Importantly, the laser beam 18 needs to be capable of altering transparent material, such as the cornea 20 of an eye, by a process known as Laser Induced Optical Breakdown (LIOB). Further, the topography sensor 16 can be a corneal topographer of any type well known in the pertinent art, that is capable of detecting aberrations in the cornea 20.

Still referring to FIG. 1, the anatomy of the anterior portion of an eye is shown to include the cornea 20 and a lens 22. The aqueous humor 24 is a clear fluid filing the space between the lens 22 and the cornea 20. Importantly, the aqueous humor 24 exerts an intraocular pressure (IOP), represented by the arrows 26, against the posterior surface 28 of the cornea 20.

Figure 2:
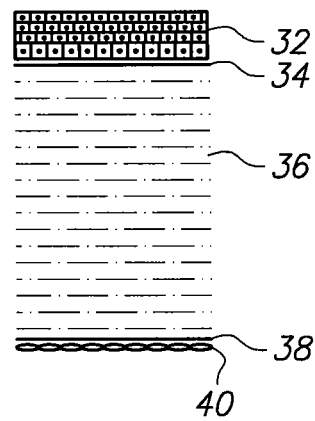
FIG. 2 is a cross section view of a cornea of an eye.

The cornea 20, as best seen in FIG. 2, includes a number of various layers. Going in a posterior direction from the anterior surface 30 of the cornea 20 toward the posterior surface 28, these various layers are: epithelium 32, Bowman's membrane 34, stroma 36, Descemet's membrane 38 and endothelium 40. Of these, the strongest tissues are Bowman's membrane 34 and the stroma 36. Bowman's membrane 34 is the strongest. The stroma 36, however, is the most responsive to the IOP 26.

Figure 3:
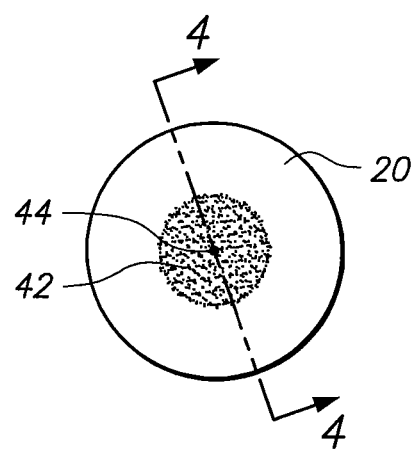
FIG. 3 is a top plan view of a cornea of an eye showing a symmetrical aberration substantially centered on the visual axis of the eye.
Figure 4A:
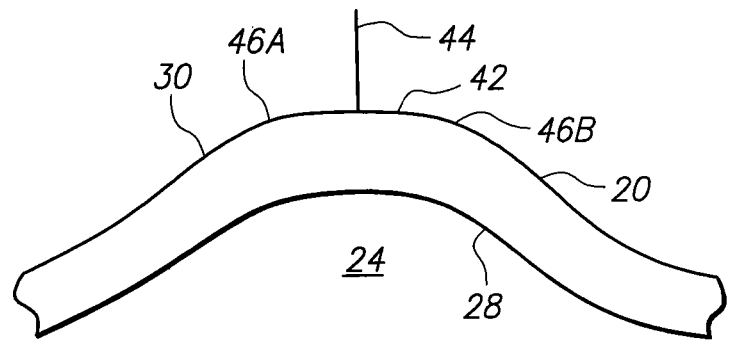
FIG. 4A is a cross section view of the cornea as seen along the line 4-4 in FIG. 3.

During the growth development of an eye, it will often happen that the cornea 20 will become somehow misshapen. This, unfortunately, will cause a person to experience vision defects that result from optical aberrations introduced by the cornea 20. For example, FIG. 3 shows a cornea 20 having an aberration (irregularity) 42 that is symmetrically oriented on the visual axis 44. With cross reference to FIG. 4A, it will be appreciated this aberration (irregularity) 42 manifests itself in the topography of the cornea 20 as a generally flat portion of the anterior surface 30. This is in contrast with a more normal, spherical shape for the topography of the anterior surface 30. A consequence of the aberration (irregularity) 42, is an annular bulge 46 that surrounds the depression (irregularity) 42 on the anterior surface 30 (i.e. the bulges 46a and 46b in cross section). In accordance with well known techniques, the aberration (irregularity) 42 can be easily identified by the topography sensor 16.

Figure 4B:
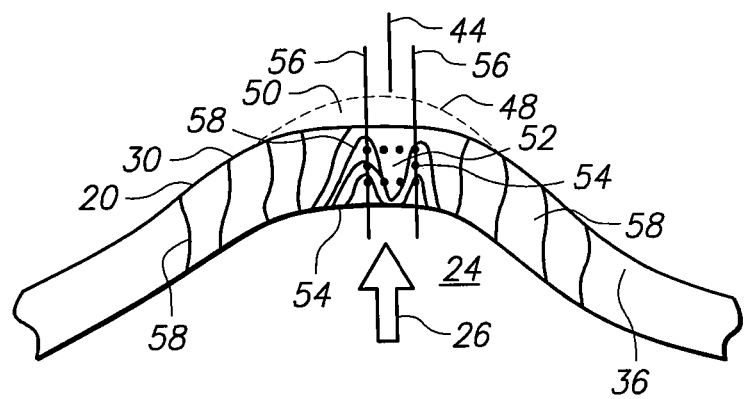
FIG. 4B is a view of the cornea shown in FIG. 4A, with superposed exemplary iso-stress lines.

Referring now to FIG. 4B, it is to be appreciated that in order to dimensionally evaluate the topography of the anterior surface 30 of cornea 20, a reference datum 48 needs to be defined for the present invention. Specifically, this reference datum 48 represents the desired configuration for the anterior surface 30; after the aberration (irregularity) 42 has been corrected. In FIG. 4B it has been indicated and shown that, for the purpose of vision correction, the reference datum 48 will preferably be a substantially spherical shaped surface. Due to the aberration (irregularity) 42, however, FIG. 4B also indicates that before the aberration (irregularity) 42 has been corrected, there will be a deviation 50 between the actual configuration of anterior surface 30, and the reference datum 48.

As envisioned for the present invention, after the aberration (irregularity) 42 has been located (such as by use of topography sensor 16), a volume of stromal tissue 52 that lies under the aberration (irregularity) 42 can be identified. An example of such an underlying volume 52 of tissue is shown bounded by the dotted line in FIG. 4B. Further, and still referring to FIG. 4B, it will be appreciated that the underlying volume 52 can be identified as having a peripheral boundary surface 54 that, in actuality, is a portion of a cylindrical surface 56. With cross reference to FIG. 3, it can be appreciated that the cylindrical surface 56 (and therefore boundary surface 54) is centered on the axis 44 and can be generally determined by the periphery of aberration (irregularity) 42.

As depicted in FIG. 4B, tissue in the stroma 36 of cornea 20 will naturally develop iso-stress lines 58 that are characteristic of stress distribution patterns. As is well known by the skilled artisan, these stress distribution patterns result from the biomechanical forces that are generated in the stroma 36. In this case, these biomechanical forces result directly from the IOP 26, and they are the reactive forces provided by the stroma 36 and Bowman's membrane 34 in response to the IOP 26. Importantly, when the cornea 20 is formed with an aberration (irregularity) 42 that is manifested by a deviation 50, the iso-stress lines 58 in the stroma 36 are distinctively different from what they would normally be. The detection of these distinctions by the topography sensor 16, or by any other well known means for determining stress distribution patterns in the stroma 36, can then be used to locate appropriate boundary surfaces 54.

Operation

Figure 4C:
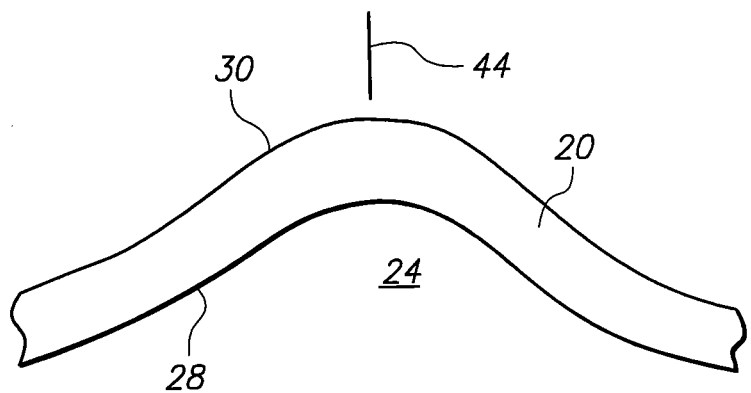
FIG. 4C is a cross section view of the cornea shown in FIG. 4A after corrective surgery in accordance with the present invention.

In the operation of the system 10 of the present invention, a device (e.g. topography sensor 16) is used to measure the topography of the anterior surface 30 of the cornea 20. Based on this measurement, irregularities in the anterior surface 30 (e.g. aberration (irregularity) 42) are observed and located. The aberration (irregularity) 42 is then compared with the reference datum 48 by the computer 14, and the deviation 50 that results from this comparison is identified. In turn, the deviation 50 is used to identify an underlying volume 52 of tissue in the stroma 36. Most importantly, depending on the dimensions and location of the deviation 50 (recall, the deviation 50 shown in the drawings is only exemplary), the boundary (interface) surface 54 is also identified. The laser unit 12 can then be employed for the LIOB of stromal tissue over the boundary surface 54, or portions of the boundary surface 54. Further, additional volumes of tissue may also be targeted. In any event, this LIOB effectively disrupts the stress distribution patterns over the boundary surface 54 and results in a significant weakening of tissue in the stroma 36 on the boundary surface 54. Stated differently, this weakening of tissue occurs between tissue in the underlying volume 52, and tissue in the stroma 36 that is not in the underlying volume 52. In response, the IOP 26 against the posterior surface 28 of the cornea 20 causes a reconfiguration of the cornea 20. Specifically, as envisioned by the present invention and shown in FIG. 4C, this reconfiguration results in a shape for the anterior surface 30 of the cornea 20 that conforms with the reference datum 48 (i.e. a substantially spherical shape). As intended, this provides the vision correction that is required.

While the particular System and Method for Altering Internal Stress Distributions to Reshape a Material as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for altering a configuration of a transparent material while the material is being subjected to an external force, the method comprising the steps of:
    measuring a topography for a surface of the material; comparing the topography with a reference datum to identify a deviation between the topography and the reference datum, the deviation selected from a group of deviations consisting of a surface bulge and a surface depression;
    identifying a volume of material underlying the deviation, wherein the underlying volume defines a boundary surface surrounding a stress distribution;
    laser cutting the material on a selected portion of the boundary surface of the underlying volume to disrupt the stress distribution causing the deviation on the selected boundary surface between material in the underlying volume and material adjacent thereto; and
    allowing the external force to alter the configuration of the transparent material in response to the cutting step.

2. A method as recited in claim 1 wherein the transparent material is a cornea of an eye.

3. A method as recited in claim 2 wherein the surface of the material is an anterior surface of the cornea.

4. A method as recited in claim 2 wherein the external force is caused by an intraocular pressure in the eye.

5. A method as recited in claim 2 wherein the reference datum is a substantially spherical surface.

6. A method as recited in claim 1 wherein the cutting step is accomplished using a femtosecond laser to cause Laser Induced Optical Breakdown (LIOB) of material.

7. A method as recited in claim 6 wherein the LIOB is accomplished over a substantially cylindrical surface.

8. A method as recited in claim 6 wherein the LIOB is accomplished over a substantially planar surface.

9. A method as recited in claim 6 wherein an extent of LIOB in the material is based on characteristics of the deviation.

10. A method for altering a configuration of a transparent material while the material is being subjected to an external force, the method comprising the steps of:
    identifying a plurality of stress distributions surrounded by a respective plurality of different boundary surfaces within the material;
    comparing each stress distribution with a reference datum to identify a deviation therebetween, the deviation selected from a group of deviations consisting of a surface bulge and a surface depression;
    selecting a boundary surface of a volume of material underlying the deviation, based on the comparing step;
    laser cutting material over the selected surface to disrupt the stress distribution causing the deviation; and
    allowing the external force to alter the configuration of the transparent material in response to the cutting step.

11. A method as recited in claim 10 wherein the transparent material is a cornea of an eye.

12. A method as recited in claim 10 wherein the cutting step is accomplished using a femtosecond laser to cause Laser Induced Optical Breakdown (LIOB) of material and the extent of LIOB in the material is based on dimensional characteristics of the deviation.

13. A method as recited in claim 12 wherein the LIOB is accomplished over a substantially cylindrical surface.

14. A method as recited in claim 12 wherein the LIOB is accomplished over a substantially planar surface.

15. A method as recited in claim 10 wherein the reference datum is a base stress distribution calculated to configure the material with a predetermined shape.

16. A device for altering a configuration of a transparent material while the material is being subjected to an external force, the device comprising:
    a diagnostic means for identifying a plurality of stress distributions surrounded by a respective plurality of different surfaces within the material;
    a computer means for selecting a surface and comparing the stress distribution on the selected surface with a reference datum to identify a deviation therebetween, the deviation selected from a group of deviations consisting of a surface bulge and a surface depression, the surface being a boundary surface of a volume of material underlying the deviation; and
    a laser means for cutting material over the selected surface, to disrupt the stress distribution causing the deviation and alter the configuration of the transparent material by allowing the material to react to the external force.

17. A device as recited in claim 16 wherein the diagnostic means is a topography sensor for measuring a topography for a surface of the material.

18. A device as recited in claim 17 wherein the reference datum is a base stress distribution calculated to configure the material with a predetermined shape.

19. A device as recited in claim 17 wherein the laser means is a femtosecond laser to cause Laser Induced Optical Breakdown (LIOB) of material.

20. A device as recited in claim 19 wherein an extent of LIOB in the material is based on characteristics of the deviation.

* * * * *